United States Patent [19]

Kambin

[11] Patent Number: 4,573,448
[45] Date of Patent: Mar. 4, 1986

[54] METHOD FOR DECOMPRESSING HERNIATED INTERVERTEBRAL DISCS

[75] Inventor: Parviz Kambin, Devon, Pa.

[73] Assignee: Pilling Co., Fort Washington, Pa.

[21] Appl. No.: 539,256

[22] Filed: Oct. 5, 1983

[51] Int. Cl.⁴ .................. A61F 17/32; A61F 5/04; A61B 17/16

[52] U.S. Cl. ................. 128/1 R; 128/305.1; 128/310; 128/92 E; 128/92 EB

[58] Field of Search .............. 128/1 R, 305, 305.1, 128/310, 303 R, 329 R, 341, 343, 328, 356, 92 E, 92 EB, 749-754, 769, 770; 604/22

[56] References Cited

U.S. PATENT DOCUMENTS

| | | | |
|---|---|---|---|
| 1,867,624 | 7/1932 | Hoffman | 128/305 |
| 2,850,007 | 9/1978 | Lingley | 128/305 |
| 3,330,278 | 7/1967 | Santomieri | 128/305 |
| 3,848,601 | 11/1974 | Ma et al. | 128/305 |
| 3,964,468 | 6/1976 | Schulz | 128/305 |
| 3,995,619 | 12/1976 | Glatzer | 128/305 |
| 4,203,444 | 5/1980 | Bonnell et al. | 128/305 |
| 4,246,902 | 1/1981 | Martinez | 128/305 |
| 4,320,761 | 3/1982 | Haddad | 128/305 |
| 4,337,773 | 7/1982 | Raftopoulos et al. | 128/305 |
| 4,444,184 | 4/1984 | Oretorp | 128/305 |
| 4,461,281 | 6/1977 | Carson | 128/305 |

Primary Examiner—Robert Peshock
Assistant Examiner—C. W. Shedd
Attorney, Agent, or Firm—Howson and Howson

[57] ABSTRACT

Decompression of herniated discs in the lumbar spine is carried percutaneously by the insertion of a specially designed cannulated trocar over a guide wire extending through the patient's back toward the herniated disc at an angle of approximately 35 degrees with respect to the patient's perpendicular line. A thin-walled cannula is passed over the trocar, and a hollow cutting instrument is inserted through the cannula to form a window in the disc. Disc fragments are removed through the cannula by means of a special punch forceps, after the application of suction to the disc nucleus through the cutting instrument.

11 Claims, 10 Drawing Figures

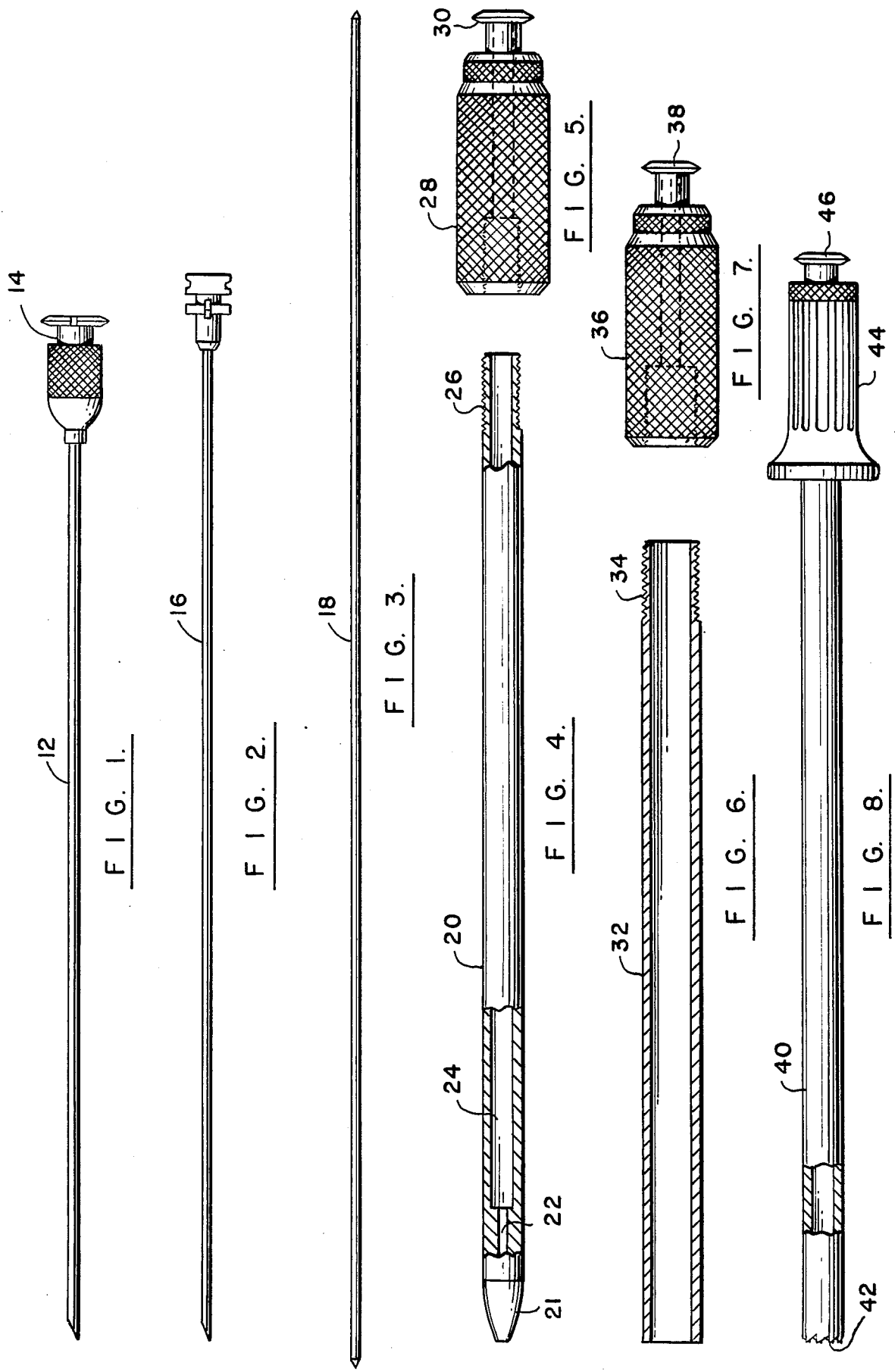

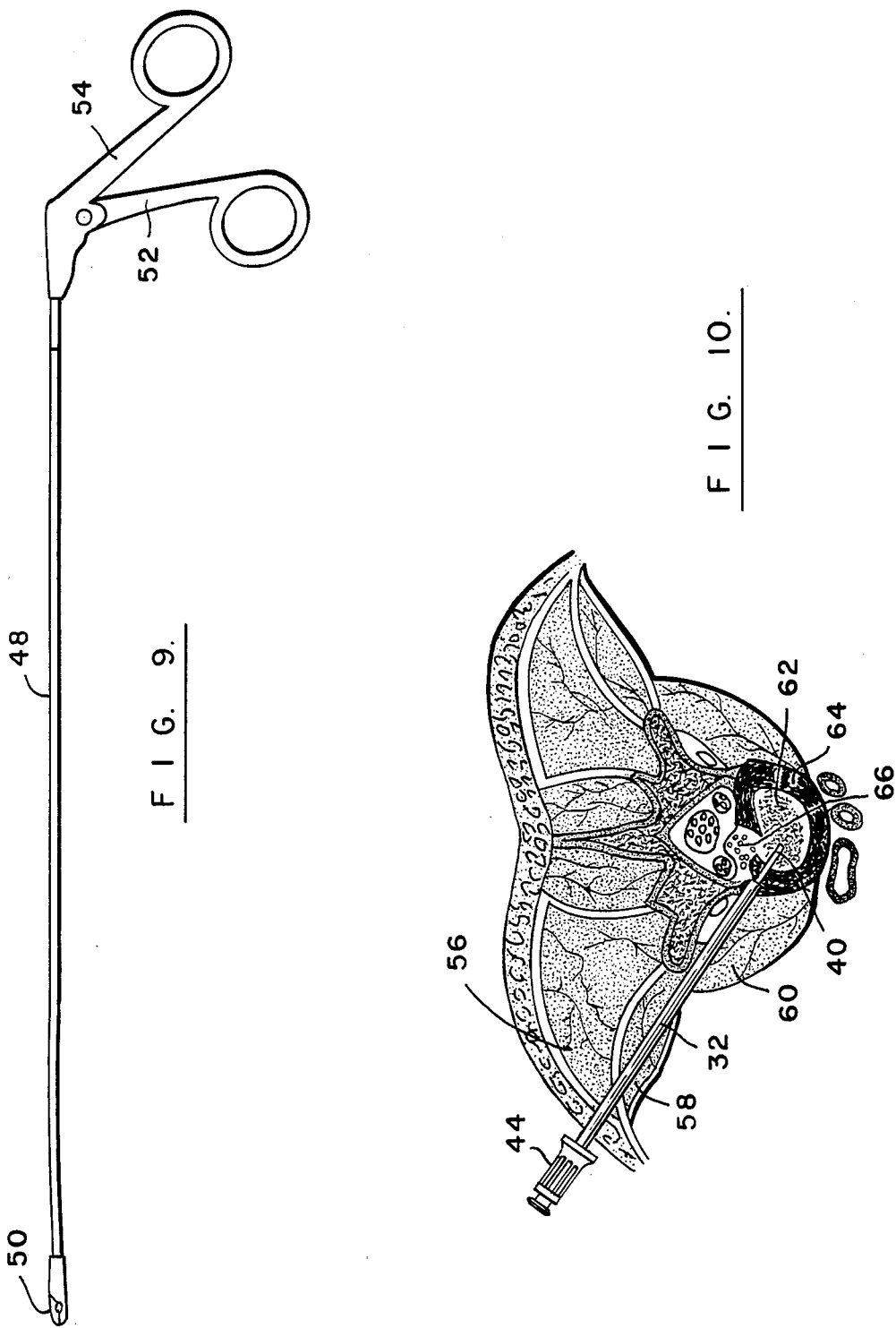

METHOD FOR DECOMPRESSING HERNIATED INTERVERTEBRAL DISCS

BRIEF SUMMARY OF THE INVENTION

This invention relates to surgery and specifically to a novel method for decompressing herniated intervertebral discs in the lumbar region of a human patient.

Low back pain syndrome with sciatica secondary to herniated intervertebral discs represents a major health probelm in the United States. An intervertebral disc is a structure which occupies the space between the vertebrae. A normal disc consists of two parts: a central part known as the "nucleus", and a surrounding part known as the "annulus" or "annulus fibrosis". The annulus degenerates with age, as does the nucleus. Degeneration of the annulus is characterized by the formation of circumferential tears in the annulus. Degeneration of the nucleus, which is initially in the nature of a colloidal gel, is characterized by collagenation, in which some of the fluid content of the nucleus is lost and fragments of collagenized fibrous tissue are formed which float in the tissue fluid. At this stage of degeneration, external forces can readily increase the hydrostatic pressure on the nucleus, causing the fibers of the annulus to rupture. Nucleus fragments protrude. This, in turn, may cause pressure on the adjacent nerve root with resultant pain.

Several methods of treatment already exist. One method, usually referred to as "laminectomy", involves the surgical excision of the herniated disc. Laminectomy is carried out by making an incision in the lower part of the spine for posterior exposure, separating the muscle from the bone, removing a portion of the vertebra, visualizing a portion of the nerve root, and surgically removing disc material. This method of treatment has been in use for nearly fifty years. Typical hospitalization time is around nine days. Recently, microsurgery has been used in the treatment of herniated discs, in a procedure known as "microlumbar discectomy". The microsurgical procedure, because it also involves posterior exposure, carries with it many of the complications associated with the older procedure, including injury to the nerve root and dural sac, perineural scar formation, reherniation at the site of the surgery, and instability due to excess bone removal.

Another recent method of treatment is known as chemonucleolysis, which is carried out by injection of the enzyme chymopapain into the disc structure. Chemonucleolysis, unfortunately, has many complications including severe pain and spasm, which may last up to several weeks following the injection. Sensitivity reactions and anaphylactic shock occur in limited but significant numbers of patients, and the death rate is around 0.5%. Other effects include disc space narrowing, requiring further treatment, and leakage of chymopapain into the subarachnoid space with damage to the thin wall vessels.

The principal object of this invention is to provide a relatively safe method for treatment of herniated discs which avoids the above-described complications and dangers of conventional surgical treatments and chemonucleolysis. It is also an object of the invention to provide a method of treatment which has the advantages of low post-operative morbidity, elimination of epidural bleeding, elimination of problems associated with reherniation, and the elimination of structural instability due to excess bone removal. It is also an object of the invention to eliminate the need for lengthy surgery in a large number of cases and to provide a cost-effective procedure for treatment of herniated discs.

The method in accordance with the invention may be carried out under local anesthesia, thus avoiding the risk of general anesthetics. In accordance with the method, a conventional hollow needle with a stylet is inserted through the skin of the patient's back at a location spaced from the midline. The needle is advanced in an oblique direction, preferably at an angle of approximately 35 degrees with respect to a line perpendicular to the patient's back, until it reaches the outside of the annulus fibrosis of the herniated disc. The stylet is then withdrawn, and a guide wire is introduced through the needle to the disc. The needle is then withdrawn, while the guide wire is held in place. A cannulated, blunt-tip trocar is passed over the guide wire until the tip reaches the outside of the annulus. The guide wire is then withdrawn. A thin-walled cannula, which closely fits over the trocar, is passed over the trocar until its distal end reaches the outside of the annulus. The trocar may then be withdrawn, and a cutting instrument inserted. The cutting instrument comprises a hollow circular cylindrical tube having cutting teeth formed in a circular configuration at its distal end. A window is formed in the herniated disc by rotary manipulation of the cutting instrument. Fragments of the herniated disc are removed through the cannula by either or both of two methods. In accordance with one method, suction is applied to the cutting instrument for the removal of disc fragments. The cutting instrument may be moved back and forth within the nucleus of the herniated disc as suction is applied. Alternatively, suction may be applied through the cannula itself. The second method is the insertion of punch forceps into the nucleus of the disc through the cannula.

As the foregoing procedures are carried out under local anesthesia, the assistance of the patient is available to assess the degree of pain relief following the removal of disc fragments. The foregoing procedures are radiographically monitored using an image intensifier. Local anesthetic can be introduced through the needle, the trocar, the cannula, and even through the cutting instrument. Special attachments are provided for introduction of anesthetic through the trocar and cannula.

BRIEF DESCRIPTION OF THE DRAWINGS

FIG. 1 is an elevational view of a needle used in accordance with the invention;

FIG. 2 is an elevational view of a stylet for the needle of FIG. 1;

FIG. 3 is an elevational view of a guide wire or "Kirschner wire" used for guiding the trocar;

FIG. 4 is a partially broken away elevational view of the trocar;

FIG. 5 is an elevational view of an anesthetic adapter for the trocar;

FIG. 6 is a longitudinal section through a thin-walled cannula in accordance with the invention;

FIG. 7 is an elevational view of a suction adapter for the cannula;

FIG. 8 is a partially broken away elevational view of the cutting instrument;

FIG. 9 is an elevational view of a punch forceps used in accordance with the invention; and FIG. 10 is a sectional view through the spinal column of a patient, showing the cannula in place, and the cutting instrument extending through the cannula into the nucleus of the patient's herniated disc.

DETAILED DESCRIPTION

FIG. 1 shows a needle 12 having a Luer lock fitting 14 at its proximal end for the introduction of a local anesthetic. The needle is a hollow, bevelled needle, typically having an external diameter of 0.050 inch and an internal diameter of about 0.038 inch. The bevel is about 23 degrees, and the length of the needle is approximately 6 inches. The needle is provided with a stylet 16, as shown in FIG. 2. The stylet is typically about 6½ inches in length, and has an external diameter of just under 0.038 inch, so that it fits within the interior of needle 12.

FIG. 3 shows a guide wire 18, which is typically about 9 inches in length, and about 0.026 inches in diameter. It has pointed ends. This wire is used to guide a special trocar toward the site of the disc.

A trocar 20, as shown in FIG. 4 has a blunt tip 21, and has a narrow passage 22 extending from the tip and meeting a larger passage 24 which extends to the proximal end. The exterior of the proximal end is threaded at 26 to receive an adapter 28 (FIG. 5), having a Luer lock fitting 30. This adapter is used for the introduction of anesthetic as the trocar is introduced. The trocar is preferably approximately 0.198 inches in diameter. Passage 22 is slightly greater in diameter than the diameter of the guide wire 18, so that it can be guided easily over the guide wire. Preferably, passage 22 is about 0.050 inch in diameter.

The thin-walled cannula 32, as shown in FIG. 6 has a threaded proximal end 34 which receives an adapter 36 (FIG. 7) having a Luer lock fitting 38. The adapter of FIG. 7 is similar to the adapter of FIG. 5 except for the size of its internal threads. It is used for the application of suction for aspiration of disc fragments through the cannula.

The exterior of the cannula is approximately 0.250 inch in diameter, while the interior is at least approximately 0.200 inch in diameter, i.e. slightly greater than the external diameter of the trocar of FIG. 4. Thus, the cannula closely fits the trocar, and can be inserted over the trocar, while the trocar is in place with its tip in contact with the exterior of the disc which is to be decompressed.

The cutting instrument of FIG. 8 comprises a hollow cylindrical tubular part 40 having saw-like teeth 42 arranged in a circular configuration at its distal end. The proximal end of the instrument is provided with a grip 44 which is used to apply a twisting motion to the instrument. The cutting instrument is hollow throughout, and is provided with a Luer lock fitting 46 at its proximal end for the attachment of a suction apparatus for aspiration of disc fragments through the cutting instrument.

The forceps of FIG. 9 are similar to a conventional punch forceps, and comprise an elongated tube 48, and jaws 50 which are controlled by manipulation of handle elements 52 and 54. Handle element 52 controls a rod which extends through tube 48 and effects pivoting motion of the upper jaw of jaws 50. The size of the tubular member and of the jaws in FIG. 9 are such as to permit insertion through cannula 32 of FIG. 6 into the nucleus of the disc through the window formed by the cutting instrument of FIG. 8.

In the procedure in accordance with the invention, the patient is placed in a prone position, and two rolled sheets which extend from ileum to the chest are placed under the patient to maintain the patient's hips in flexion to prevent undue pressure on the abdomen and to reduce tension on the sciatic nerve. The patient's knees are also kept in flexion by extra supports under the legs. This position is used to minimize movement of the patient during the procedure and to maintain the patient as comfortable as possible.

The operation is carried out under continuous radiographic monitoring using a C-arm image intensifier. The lumbar area is prepared and draped in the usual manner, and anesthesia is induced by local infiltration of a 0.5% Xylocaine solution.

The skin is punctured about 3.5 to 4 inches from the midline by needle 12 with stylet 16 in place within the needle. The needle is introduced from the side in which radicular pain and neurologic deficit are present. The needle is inserted at an angle of approximately 35 degrees with respect to a line perpendicular to a patient's back. The transverse process is bypassed, and the needle is advanced to the intervertebral disc space. The needle can be redirected if radicular pain is encountered.

When the needle is correctly positioned and in contact with the exterior of the disc, stylet 16 is withdrawn and replaced with guide wire 18. The needle is then withdrawn while the guide wire is held in place. The trocar 20 of FIG. 4 is then passed over the guide wire with a twisting motion until it reaches the location of the exterior of the annulus. Xylocaine may be introduced through the trocar as needed, using the adapter of FIG. 5.

The use of a guide wire together with a cannulated trocar is particularly important to the success of this procedure because of the large diameter of the trocar (typically 0.198 inch) dictated by the necessarily large internal diameter (typically 0.200 inch) of the thin-walled cannula. Because of the large diameter of the trocar, it is very important that it be guided properly to avoid irreversible nerve damage.

After the trocar is properly positioned, the guide wire is removed, and cannula 32 is passed over the trocar. When the cannula is in place, it is held firmly against the annulus to prevent it from slipping. The trocar is then withdrawn, and the cutting instrument of FIG. 8 is introduced. The length of the cutting instrument is such that it can extend approximately 0.8 inch beyond the end of the cannula when fully inserted. The cutting instrument is manually rotated until a window is formed in the annulus.

As shown in FIG. 10, cannula 32 extends through the sacro spinalis 56, through the quadratus lumbrum 58, and through the psoas major 60 to the exterior of annulus 64 of the disc. The tubular part 40 of the cutting instrument extends into the nucleus 62 of the disc, and suction is applied to the nucleus by aspiration through the cutting instrument. In many cases excellent results are achieved by applying suction through the cutting instrument while the cutting instrument is moved back and forth by manipulation of grip 44. As the disc is decompressed, the herniation 66 recedes, and fragments are moved to positions within the disc from which they can be withdrawn. Withdrawal of fragments is carried out by using the punch forceps of FIG. 9, which can be inserted through cannula 32 after the cutting instrument is removed. In some cases, fragments can be withdrawn by aspiration through the cutting instrument or through the cannula.

In some cases, it is possible to position the instruments so that the cutting instrument enters the bulge of herniation, in which case the disc fragments can be withdrawn directly.

The procedure described above, by virtue of the postero-lateral approach, avoids the need for bone removal and the resultant complications. As in the case with conventional laminectomy, reherniation through the operatively produced annulus fenestration may occur. However, the location of the fenestration produced in accordance with this new method is such that reherniation is much less likely to apply pressure to the patient's nerve roots.

I have found that patients treated in accordance with this new procedure are generally able to ambulate and sit on the day of surgery or one day afterward, and that post-operative back pain was minimal and controllable by oral medication. Hospitalization time with this new procedure is typically two days.

I claim:

1. A method for decompressing a herniated intervertebral disc in the lumbar region of a human patient comprising the steps of:
    inserting a hollow needle with a stylet through the skin of the patient's back at a location spaced from the midline of the back and advancing the needle in an oblique direction with respect to a line perpendicular to the patient's back until it reaches the outside of the annulus fibrosis of the herniated disc;
    withdrawing the stylet;
    introducing a guide wire through the needle to the disc;
    withdrawing the needle;
    passing a cannulated, blunt-tipped trocar with an opening in its tip slightly greater in diameter than the diameter of the guide wire, over the guide wire until the tip reaches the outside of the annulus fibrosis of the herniated disc;
    withdrawing the guide wire;
    passing a thin-walled cannula which closely fits the trocar, over the trocar until the distal end of the cannula reaches outside of said annulus;
    withdrawing the trocar;
    introducing through the cannula a cutting instrument comprising a hollow circular cylindrical tube having cutting teeth formed in a circle on its distal end;
    with the cannula still in place, forming a window in the herniated disc by rotary manipulation of the cutting instrument; and
    with the cannula still in place, evacuating fragments of the herniated disc through the cannula.

2. A method according to claim 1 in which the oblique direction in which the needle is advanced is at an angle of approximately 35 degrees with respect to the perpendicular line of the patient.

3. A method according to claim 1 in which anesthetic is introduced through the trocar as the trocar is passed over the guide wire toward the herniated disc.

4. A method according to claim 1 in which the internal diameter of the thin-walled cannula is at least approximately 0.2 inch.

5. A method according to claim 1 in which the step of withdrawing the trocar is carried out while holding the cannula firmly against the outside of the annulus fibrosis of the herniated disc.

6. A method according to claim 1 in which the cutting instrument is withdrawn from the cannula, with the cannula still in place, and in which evacuation of fragments is carried out using a punch forceps extending through the cannula.

7. A method according to claim 1 in which the evacuation of fragments is carried out by aspiration through the cannula.

8. A method according to claim 1 in which the evacuation of fragments is carried out by aspiration through the cutting instrument.

9. A method according to claim 1 in which the evacuation of fragments is carried out by aspiration through the cutting instrument while the distal end of the cutting instrument is moved back and forth within the nucleus of the herniated disc.

10. A method according to claim 1 in which the evacuation of fragments is carried out by a punch forceps extending through the cannula following the application of suction to the nucleus through the cutting instrument.

11. A method according to claim 10 in which the distal end of the cutting instrument is moved back and forth within the nucleus of the herniated disc while suction is applied.

* * * * *

UNITED STATES PATENT AND TRADEMARK OFFICE
CERTIFICATE OF CORRECTION

PATENT NO. : 4,573,448
DATED : March 4, 1986
INVENTOR(S) : Parviz Kambin

It is certified that error appears in the above-identified patent and that said Letters Patent is hereby corrected as shown below:

Kindly amend the face of the patent document by inserting the following -- OTHER REFERENCES CITED "Percutaneous Lateral Discectomy of the Lumbar Spine", Parviz Kambin, M.D. and Harris Gellman, M.D., April, 1983. --

Signed and Sealed this

Sixth Day of November, 1990

*Attest:*

HARRY F. MANBECK, JR.

*Attesting Officer*  *Commissioner of Patents and Trademarks*